United States Patent [19]

Heckele

[11] Patent Number: 5,448,989
[45] Date of Patent: Sep. 12, 1995

[54] MEDICAL INSTRUMENT SHAFT CAPABLE OF POSITIVE AND NON-POSITIVE LINKING OF SEGMENTS

[75] Inventor: Helmut Heckele, Knittlingen, Germany

[73] Assignee: Richard Wolf GmbH, Knittlingen, Germany

[21] Appl. No.: 200,082

[22] Filed: Feb. 18, 1994

[30] Foreign Application Priority Data

Feb. 22, 1993 [DE] Germany ............... 43 05 376.9

[51] Int. Cl.$^6$ .............................................. A61B 1/008
[52] U.S. Cl. ................................. 600/142; 604/282; 600/104; 600/149
[58] Field of Search ............. 128/4.5, 6, 656, 658; 604/282, 95; 403/43

[56] References Cited

U.S. PATENT DOCUMENTS

| | | | |
|---|---|---|---|
| 3,557,780 | 1/1971 | Sato | 128/4 |
| 4,375,818 | 3/1983 | Suwaki et al. | 128/4 X |
| 4,655,257 | 4/1987 | Iwashita | 128/4 X |
| 4,807,596 | 2/1989 | Hochberger et al. | 128/4 |
| 4,873,965 | 10/1989 | Danieli | 128/6 |
| 5,105,819 | 4/1992 | Wollschläger | 128/4 X |
| 5,143,475 | 9/1992 | Chikama | 128/4 X |
| 5,174,277 | 12/1992 | Matsumaru . | |
| 5,179,935 | 1/1993 | Miyagi | 128/4 |
| 5,251,611 | 10/1993 | Zehel et al. | 128/4 |
| 5,271,382 | 12/1993 | Chikama | 128/4 |
| 5,299,559 | 4/1994 | Bruce et al. | 128/4 |

FOREIGN PATENT DOCUMENTS

| | | | |
|---|---|---|---|
| 3039551 | 10/1981 | Germany | 128/4 |
| 3602092 | 8/1986 | Germany . | |

*Primary Examiner*—Richard P. Apley
*Assistant Examiner*—John P. Leubecker
*Attorney, Agent, or Firm*—Panitch Schwarze Jacobs & Nadel

[57] ABSTRACT

A shaft for medical instruments, especially for guiding instruments into body cavities, has neighboring segments that are hollow on the inside and that form sections of the shaft. The segments can be adjusted in their positions by means of control wires so that various shaft curvatures can be set, whereby at least two groups of segments can be adjusted independently of one another. The segments of a first group, provided distally, are flexibly linked with each other. A tensioning device provides a variably adjustable spring force to the segments of the second group such that when under low tension, the segments are non-positively locked, and under high tension, the segments are positively locked.

20 Claims, 8 Drawing Sheets

MEDICAL INSTRUMENT SHAFT CAPABLE OF POSITIVE AND NON-POSITIVE LINKING OF SEGMENTS

FIELD OF THE INVENTION

The invention is based on a shaft for medical instruments, in particular one for guiding instruments into a body cavity. For the purpose of setting shaft curvatures, neighboring segments that are hollow on the inside and form sections of the shaft are adjustable in their position by means of control wires, whereby at least two groups of segments are adjustable independently of one another.

BACKGROUND OF THE INVENTION

In cases of medical intervention in which an instrument has to be inserted into a body cavity, it is often expedient to guide the instrument by means of a flexible shaft, since in many cases treatment is very difficult otherwise, and the use of flexible instruments causes the patient less pain than the use of rigid instruments. Thus, it is often necessary during endoscopic diagnosis and therapy, for example, to be able to bend at least the distal end of the instruments used in different directions inside the body cavity, and in addition, to be able to leave the shaft in this bent position.

For example, according to DE-AS 1 019 048, it is known that a thin-walled instrument shaft can be bent into the desired shape before use and can then, for example, be guided into a body cavity. However, a disadvantage of an instrument of that type is that it can only be inserted in a limited way, since the position that is set once before the treatment cannot be further altered.

Beyond that, bendable arrangements of tubes and shafts for use in an endoscope, especially for example in the area of bronchoscopy, are known in which the arrangement of tubes has, at least in part, regions of segments that are arranged together in a series and that are movable against each other, whereby for the purpose of setting shaft curvatures, the segments can be moved by means of control wires that are guided into a handle. Examples of these are set forth in DE-GM 69 38 905, U.S. Pat. No. 3,190,286, DE-AS 1 291 437, DE-OS 1 766 209, DE-AS 1 816 973, and DE-OS 1 950 035. In the case of DE-AS 1 816 973, the individual segments of the shaft are linked with one another by means of forks that interlock when the components are joined together. A solution of that type proves to be disadvantageous, since the forks of the segments can easily break or become deformed.

These solutions can be used with varying degrees of success for endoscopy, but they all have the disadvantage that when they are in the distorted state, that is when the curvature of the distal end of the shaft has been established and manipulation of instruments is to be undertaken in the body cavity, no real rigidity of the shaft can be attained, and, due to the unavoidable effects of forces on the shaft from the instrument that has been guided into position, the shaft can easily deviate from the desired position.

With these shafts the characteristics of a rigid shaft cannot be attained, while pre-curved shafts, such as those known from DE-AS 1 019 048, can be used only in a limited manner since they retain during use the shape that was set ahead of time. For that reason, the solution in accordance with DE-OS 1 766 209, in which the groups composed of individual segments can be moved independently of each other by means of wires, is better overall. However, the position that is set cannot be fixed with this solution.

SUMMARY OF THE INVENTION

An object of the invention is to provide a shaft for medical instruments, particularly, for guiding of instruments into a body cavity, the curvature of which shaft can easily be changed upon introduction into a body cavity and during the examination of a body cavity, and that, in addition, can be set, that is fixed, in a working position in such a way that it can be handled like a rigid shaft.

This object is achieved in accordance with the invention by providing in the shaft mentioned in the Field of the Invention, the segments of a first distal group, flexibly linked with each other, the proximally adjoining segments of a second group being linked in a non-positive manner and being tensioned by means of a variably adjustable spring force.

The advantage of this solution in accordance with the invention lies in the fact that the segments of the groups can be adjusted independently of one another. In addition, the distal part of the shaft can be set and/or adjusted before and during the use in a body cavity, so that it can always be adapted to existing conditions, while the segments of the proximal part of the shaft can be so strongly tensioned that this part of the shaft is rigid.

Furthermore, the sediments of the second group are held together by tensioning wires that are fixed in an advantageous manner in a tensioning device inside the handle of the instrument. Based upon a particular embodiment of these segments, when there is very strong tension on them, they are no longer held in place in the non-positive manner that exists when they are under low tension, but are instead held in place by means of positive locking.

In addition to the tensioning device inside the handle, adjustment devices are also provided for the segment groups, so that independent adjustment of the two groups can be carried out. The adjustment of the individual segments takes place by means of control wires that run through the segments. For each of the two groups, two control wires are provided, which terminate in the associated adjusting devices in the handle. Depending on the arrangement of the control wires within the segments of the two groups, the entire shaft can ultimately be moved in either one or two planes. In addition, several groups with differing segments can be placed in a series one behind the other so that the shaft can be curved in different ways at several sections. The handle should then be equipped with adjusting devices in an appropriate manner. Further advantageous embodiments of the invention are described below.

BRIEF DESCRIPTION OF THE DRAWINGS

The foregoing summary, as well as the following detailed description of preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION OF PREFERRED EMBODIMENTS

Figure 1:
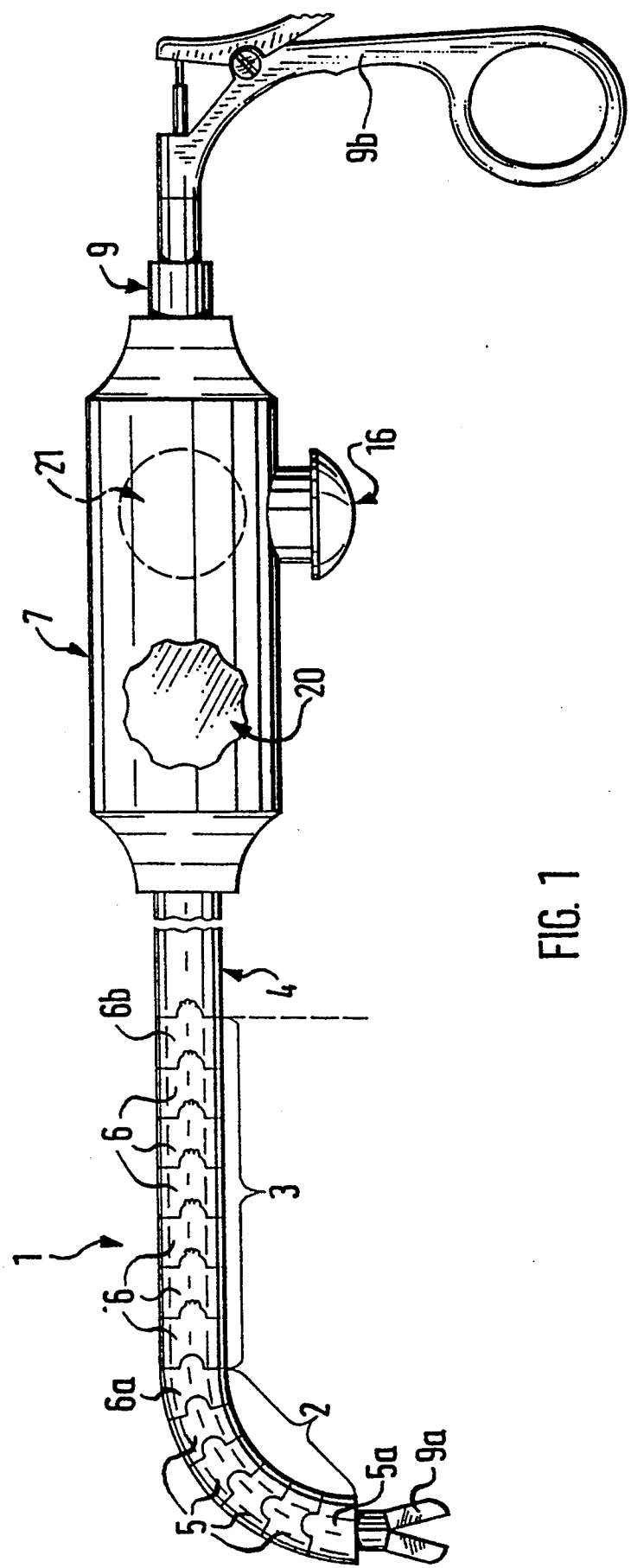
FIG. 1 is a full view of a shaft according to the invention with an inserted instrument.

In the embodiment of FIG. 1, the shaft 1 in accordance with the invention exhibits over its length three different shaft sections, which are hollow on the inside. A handle 7 is provided proximally. A first, distal segment group 2 made up of individual segments 5 represents the first shaft section. The segments 5 are flexibly linked with one another, and they can be adjusted in their position by means of control wires 10, 11 (see FIGS. 2 and 7) for the purpose of setting shaft curvatures. To the proximal end of the first, distal group 2, there is joined a second segment group 3, which is likewise made up of individual segments 6. These segments 6 differ in their manner of construction from those in the first group 2, concerning which more detail is provided in the description of FIGS. 2, 7, and 8. The segments 6 of the second group 3 are linked with one another in a non-positive manner, and are tensioned by means of a variably adjustable spring force. The segments of both groups 2 and 3 are adjustable independently of one another. In addition, the segments 5, 6 are enclosed by a flexible tube as an outer covering.

It goes without saying that the number of groups does not have to be limited to the two that are shown in this embodiment. There is also the possibility of providing several groups of segments, one after the other, that can be adjusted independently of one another, by means of which the shaft can be curved in different ways in three or more sections. Independent of the number of groups, there is attached to the last proximal group a shaft section (in this embodiment shaft part 4), which is rigid in the usual manner and which ends in the handle 7. An instrument 9 for the treatment of the patient can be fed through the interior lumen 8 of the shaft 1. In FIG. 1, such an instrument 9 is indicated by means of its distal end 9a and its handle 9b.

FIG. 1 also shows the handle 7 of the shaft 1. This handle contains the various devices for the setting and adjusting and for tensioning of the segments 5 and 6 of the groups 2 and 3. The handle 7 is also hollow on the inside in known fashion in order to be able to feed the instrument 9 all the way through. The handle 7 has an adjusting device 20 which is used to adjust the curvature of the shaft in the region of the first, distal group 2 by means of the control wires 10 and 11. In an analogous manner, a second adjusting device 21 is provided (shown by dotted line in FIG. 1), which is used to adjust the curvature of the segments 6 of the second group 3 by means of the control wires 12 and 13. If more groups of segments are provided that can be adjusted in their positions independently of one another, then a corresponding number of adjusting devices can be provided in the handle 7. Finally, handle 7 also has a tensioning device 16 for fixing the various positions of the segments 6, which are held together by means of tensioning wires 14 and 15.

Figure 2:
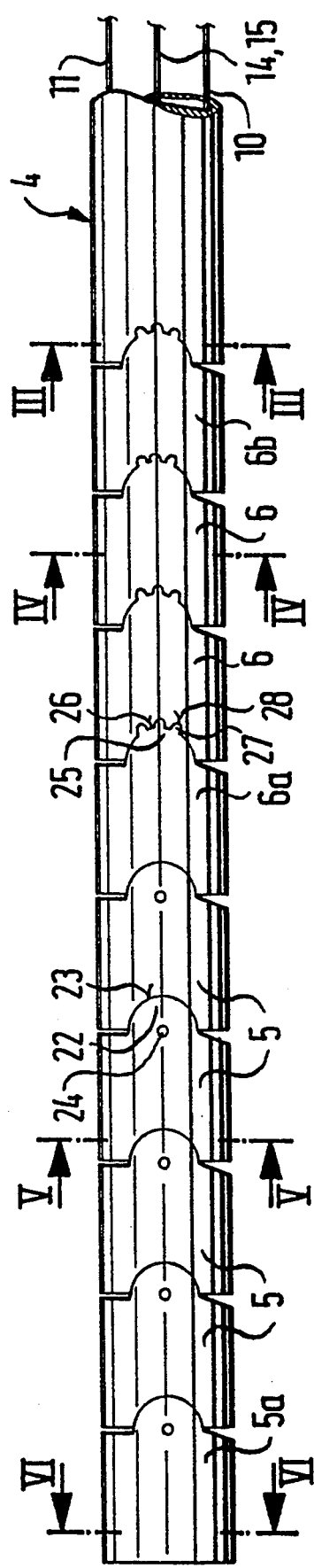
FIG. 2 is an enlarged partial view of the shaft.
Figure 3:
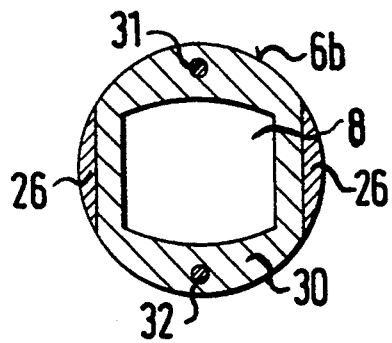
FIGS. 3–6 are sections of the shaft taken along lines III—III, IV—IV, V—V, VI—VI, respectively, in FIG. 2.
Figure 4:
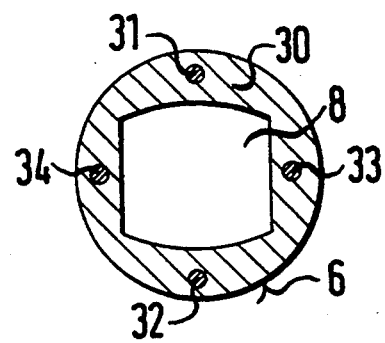
Figure 5:
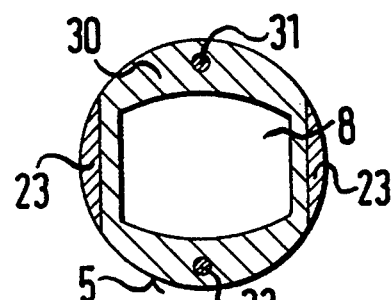
Figure 6:
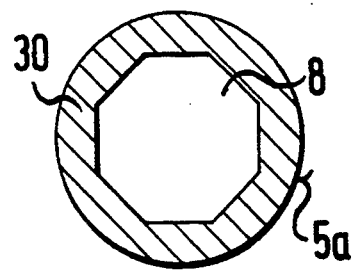

FIGS. 2 through 8 and 10 through 12 make clear the embodiments of the segments 5 and 6 which are configured differently. The segments 5 of the group 2 have at one end semicircular projections 22, and at the other end, matching recesses 23, which lie diametrically opposed to each other, as is shown in section in accordance with FIG. 7 and in FIG. 10. Segments 5 that are configured in that way, can be joined together because of their shape into one shaft section when the two projections 22 of one segment 5 are inserted into the corresponding recesses 23 of an immediately following segment 5. Two segments 5 are connected with each other in an axially flexible manner by means of lateral connecting pieces 24, which could be pins or rivets for example. The last distal segment 5a, (as seen in FIG. 2), can be closed off with a flat surface, which forms the distal end of shaft 1. In addition, the control wires 10 and 11 are secured at this last segment 5a, as FIG. 7 makes clear.

Figure 11:
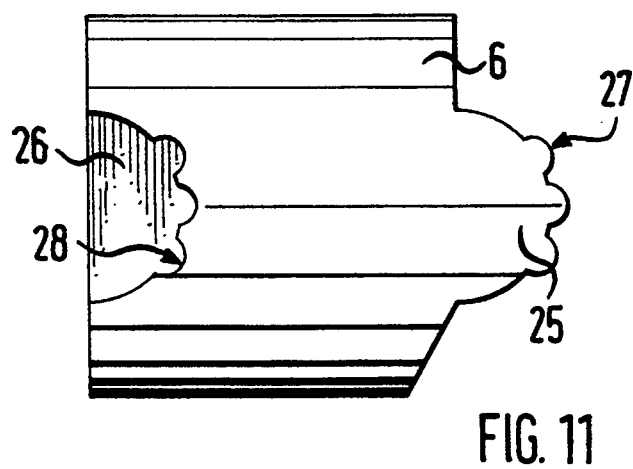

In a manner similar to that of the segments 5 of the first group 2, the segments 6 of the second group 3 also exhibit at one end semicircular projections 25, and at the other end matching recesses 26, which lie diametrically opposed to each other in accordance with FIGS. 2 and 11. The contours of the projections 25 and the recesses 26 are in the shape of a wavy line, so that when the segments 6 are joined together, the wave crests 27 of the projections 25 of a segment 6 always interlock in the wave troughs 28 of the recesses 26 of the next sequential segment 6. Alternatively or additionally, there exists the possibility of shaping the recesses of the segments 6 in the same way as those of the segments 5 of the first group 2, and to provide a lock pin in the middle of the bowed line of each recess 26, so that when the segments 6 are joined together, each projection 25 of a segment 6 works in combination with the lock pin of the next sequential segment 6.

Figure 12:
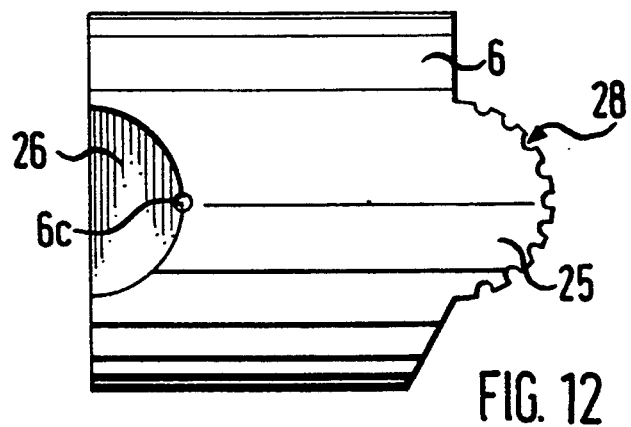
Figure 13:
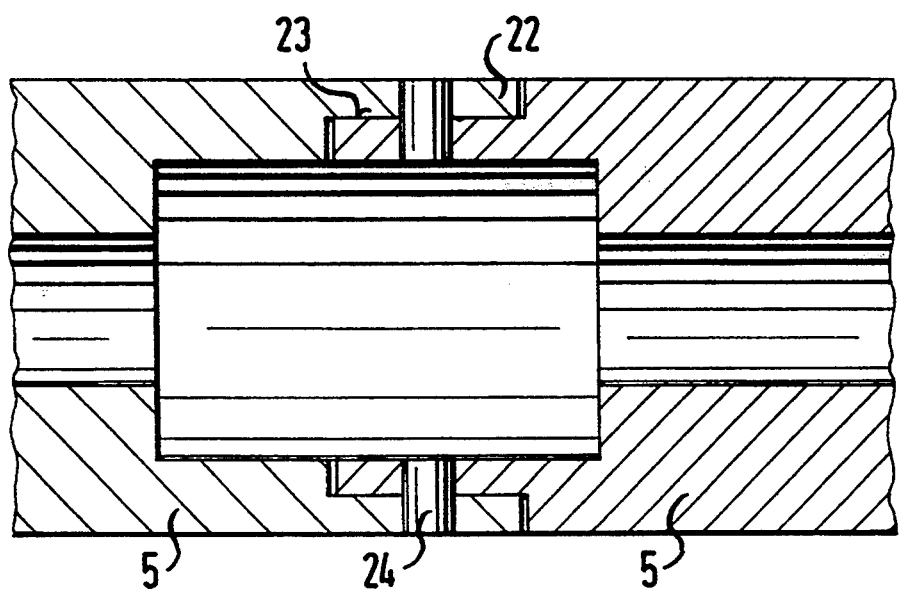
FIG. 13 shows a section through the shaft in the region of two adjoining segments.

An additional possibility for locking the segments 6 with lock pins is shown in FIG. 12. Here, the segments 6 are equipped with wavy line-like projections 25 at one end and with lock pins 6c at the other end. In this way, the lock pins 6c of one segment can work in combination with the projections 25 of another segment, in which case, depending on the positioning of the two segments relative to each other, the lock pins lock in one of the wave troughs 28 of the neighboring segment.

The distally last segment 6a of the second group 3 is connected with the proximally first segment 5 of the first group 2 in an axially flexible manner, for example by means of rivets 24. To receive the projections 25 of the proximally last segment 6b, the distal end of the rigid shaft part 4 is provided with recesses 26 that correspond to those of the segments 6, and depending on the particular embodiment, either exhibits a lock pin or is made in the shape of a wavy line.

The length of each of the groups that make up the shaft (in this embodiment, groups 2 and 3), can be established in accordance with the conditions of the treatment, that is, in accordance with the insertion site and the nature of the instruments to be inserted, by selecting an appropriate number of segments 5 and/or 6 to be arranged in a series one after the other.

Figure 7:
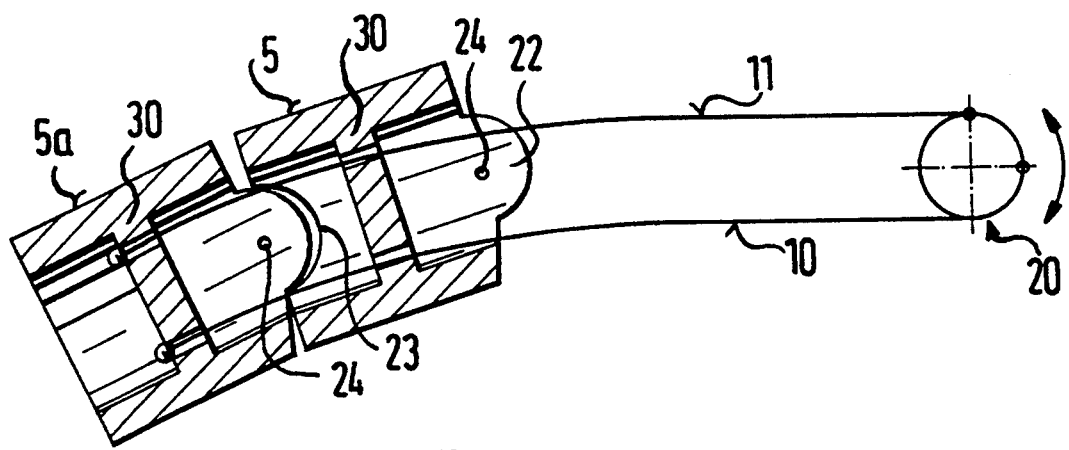
FIG. 7 is a section of the shaft shown in FIG. 1, partially in section.

FIG. 7 shows the course of the control wires 10 and 11 of the segments 5, which wires continue in the proximal direction to the adjusting device 20, where they are fastened. The control wires 10 and 11 run through bores 31 and 32 (see FIGS. 3-5) inside the wall 30 of the segments 5 and 6 of the two groups 2 and 3. Adjusting devices of this type are known, so that they can be made as in DE-OS 1 766 209 or as a simple winch in accordance with U.S. Pat. No. 3,190,286. The same holds true for the adjusting device 21. A description of such an adjusting device is therefore omitted.

Figure 8:
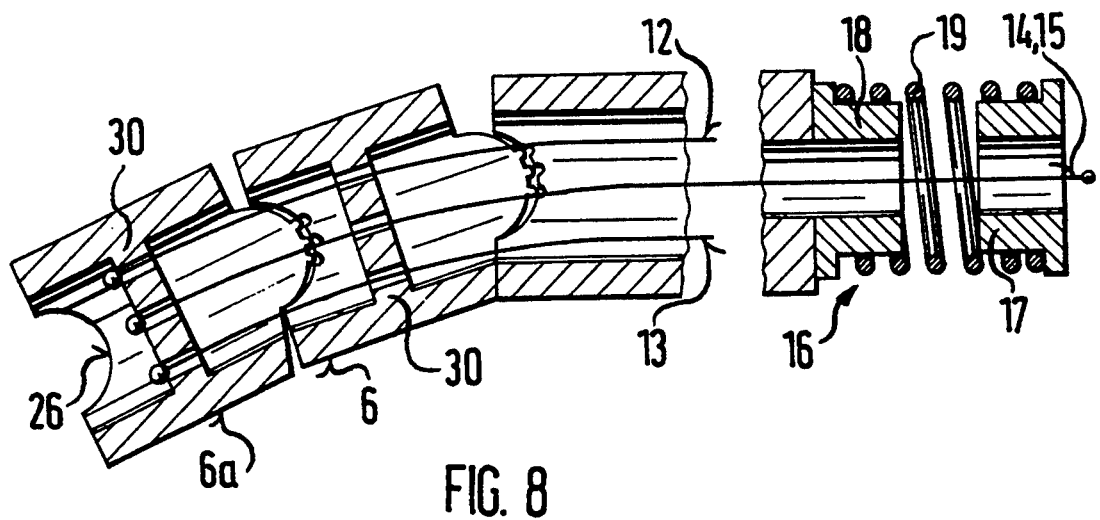
FIG. 8 is another section of the shaft shown in FIG. 1, in section.

The segments 6 of the second group 3 are similarly adjusted by means of control wires 12 and 13, which, in accordance with FIG. 8, are secured at segment 6a and, in a manner analogous to that of control wires 10 and 11 of the segments 5, run through bores of the segments 6 and are guided to the additional adjusting device 21. The control wires 12 and 13 can, for example, be fed along with the control wires 10 and 11 or along with the tensioning wires 14 and 15 through the appropriate bores 31 and 32 or 33 and 34, so that no additional bores are necessary. If the control wires 12 and 13 are run along with the control wires 10 and 11 through the bores 31 and 32, then the adjustment of the entire shaft 1 in one plane is possible. If the control wires 12 and 13 are run through the bores 33 and 34 (see FIG. 4), the adjustment of the entire shaft 1 in two planes is possible.

The tensioning wires 14 and 15 that run through the bores 33 and 34 of the segments 6 are secured proximally in a tensioning device 16, while the distal ends of the tensioning wires 14 and 15 are fastened at segment 6a.

Figure 9:
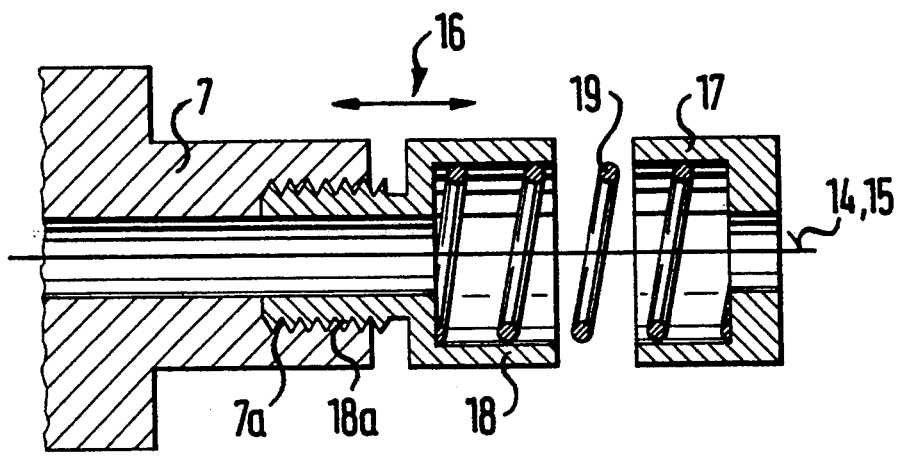
FIG. 9 shows a tensioning device for shaft segments.
Figure 10:
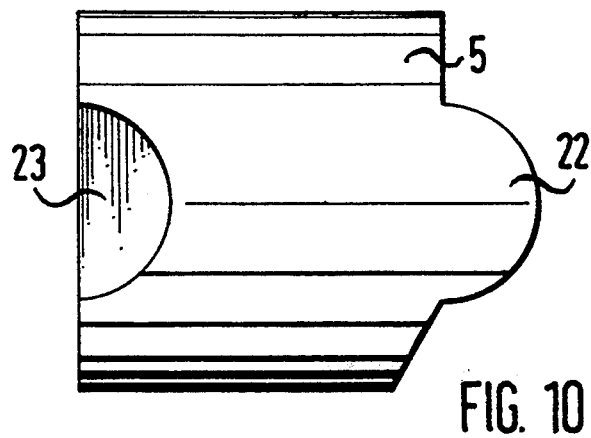
FIGS. 10–12 show different embodiments of shaft segments in side view.

The tensioning device 16, as represented in FIG. 9, can simply consist of two seats 17 and 18 for a spring 19, for example a coil spring, which as a pressure spring holds the two seats 17 and 18 at a distance from one another. The tensioning wires 14 and 15 are fed through the two seats 17 and 18 and the spring 19 and are secured at the proximal seat 17. The distal seat 18 has a threaded region 18a, by means of whose adjustment within a counter-thread 7a in the handle 7, a setting of the tension of the segments 6 takes place by changing the distance between the seats and therefore the spring tension and the tensile force of the tensioning wires 14, 15 that hold the segments 6 together.

Under low spring loading, the interlocking of the projections and recesses of the segments 6 leads to a non-positive connection. That is, a movement of the segments 6 against each other and against the rigid shaft part 4 is still possible when there is a temporary suspension of the interlocking connections between the segments that remain under the low spring tensioning. Thus, the shaft section that is formed by the segments 6 can, for example, be pre-shaped by hand before its introduction into a body cavity, and then by adjusting and increasing the spring pressure by means of the tensioning device 16, a completely rigid shaft section can be attained, while the shaft section formed by the segments 5 remains adjustable.

In addition, there is also the possibility of setting shaft 1 completely rigid in a straight state, bringing it to the site of the treatment, and then adapting its curvature to the given conditions. In order to do this, the spring pressure as described above is first adjusted for setting the segments 6 of the second group 3, and the control wires 10 and 11 are drawn tight. In this way, a totally rigid shaft 1 can be attained. Inside the body cavity, the rigid state can then be relieved by reversing the procedure described above.

When this is done, the segments 5 of the first group 2 can be adjusted with the control wires 10 and 11 for the purpose of setting the necessary shaft curvature. When there is a correspondingly severe curvature of the first, distal group 2, by overcoming the non-positive connection caused by the low spring loading described above, the segments 6 can take part in the curvature and lock into a new position. However, the possibility of an independent adjustment of the segments 6 proves to be advantageous, and this is accomplished by then providing the additional control wires 12 and 13.

If the tensioning wires 14 and 15, which hold the segments 6 together by means of the tensioning device 16 via the adjustment of the seat 18 inside the handle 7, are extremely strongly tensioned, then the wave peaks 27 of the projections 25 of a segment 6 mesh into the wave troughs 28 of the recesses 26 of the next-following segment 6 in such a way that the segments 6 are held together by means of a positive locking, and not just by the non-positive connection as is the case at lower tension. The same naturally holds true for the possible alternative embodiments of segments 6 that make use of lock pins.

Figure 14:
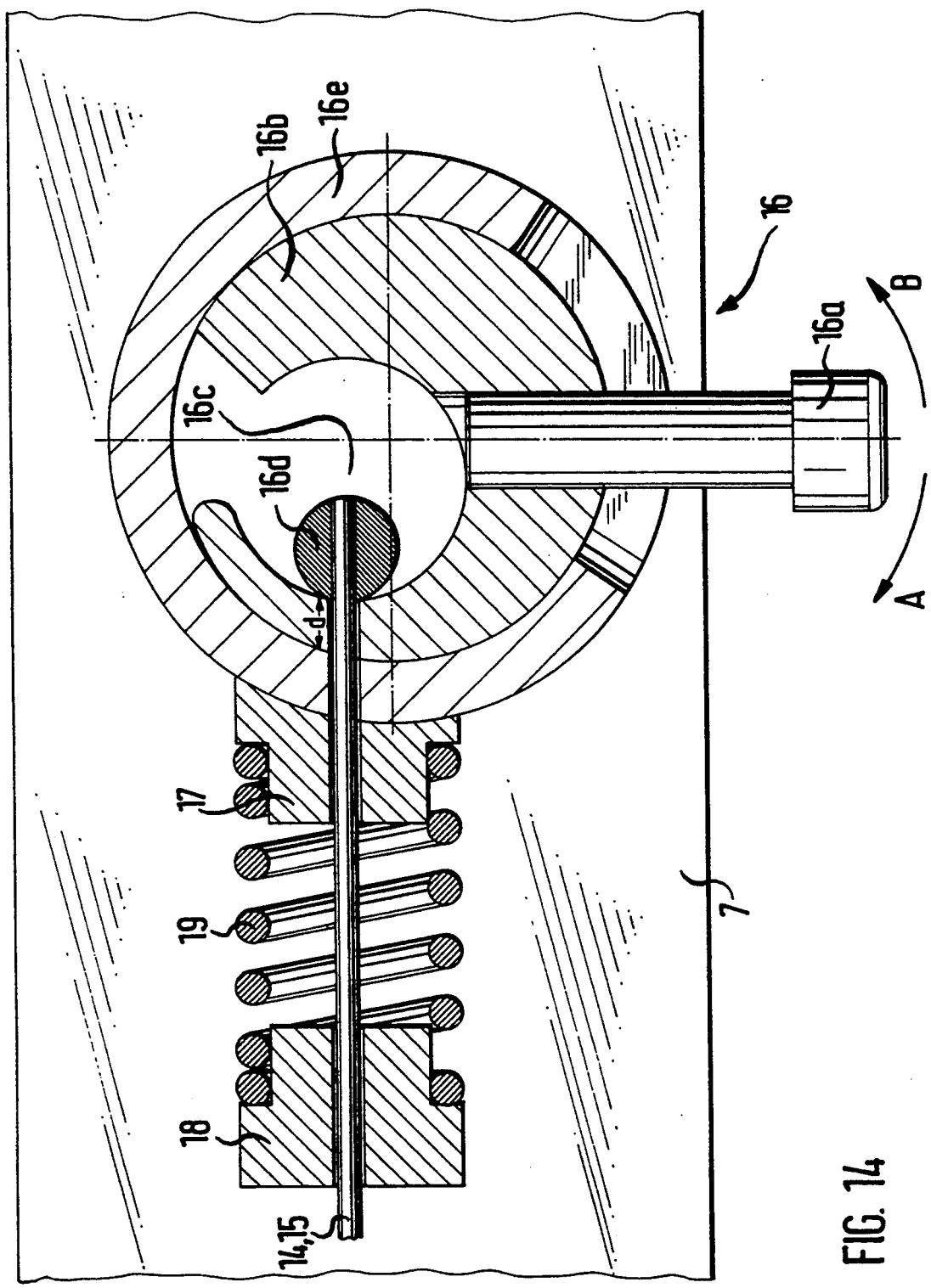
FIG. 14 is a device for tensioning of shaft segments.

A tensioning of the segments 6 that can be carried out easily and especially quickly can be attained by means of the tensioning device shown in FIG. 14, in which the same or like-working parts are used as in the tensioning device shown in FIGS. 8 and 9. For this reason, these parts and the tensioning device in FIG. 14 are provided with the same, corresponding reference numerals.

With the tensioning device 16 that is mounted inside the handle 7 shown in FIG. 14, the tensioning wires 14, 15, which are pre-tensioned by the spring 19, can be drawn so tight that the shaft part made up of the segments 6 becomes practically rigid. In order to do this, a disc 16b is provided having an eccentric bore 16c, inside of which the ends of the tensioning wires are fastened, for example by means of a ball 16d. Disc 16b is adjusted or turned inside of a housing 16e by means of an adjusting lever 16a that comes out of the handle. When the adjusting lever 16a is moved in direction A, that is towards the distal end of the shaft, the tensioning wires are drawn in a proximal direction as a result of the increasing distance d and the segments 6 are placed under tension, while in the opposite direction, that is when the adjusting lever 16a is moved in direction B, the tension in the tensioning wires is lowered and the forces holding the segments 6 together are reduced.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A shaft (1) for guiding medical instruments, particularly for guiding instruments into a body cavity, comprising at least a first group (2) of neighboring segments (5) and a second group (3) of neighboring segments (6), said segments (5, 6) being hollow on their insides, control wires (10, 11; 12, 13) connected respectively to said first and second groups for adjusting positions of said segments, and means for adjusting the segments of one group independently of another group, said shaft having distal and proximal end regions, the segments (5) of the first group (2) being provided in the distal end region and being flexibly linked with each other, the segments (6) of the second group (3) being provided proximally of the first group (2) and including means for axially linking the segments (6) of the second group (3) together, and a spring (19) connected to the segments (6) of the second group (3) and having variably adjustable force for tensioning the segments (6) of the second group (3), whereby the positions of the segments (5,6) may be set to form various curvatures of the shaft, and wherein the segments (6) of the second group (3) have at one end semicircular projections (25) that lie diametrically opposed to each other, each projection having a circumference formed in the shape of a wavy line with wave crests (27) and wave troughs (28), and at the other end matching recesses (26), whereby the wave crests (27) of the projections (25) of a segment (6) always interlock in the wave troughs (28) of the recesses (26) of a neighboring segment (6).

2. The shaft in accordance with claim 1 wherein the segments (6) of the second group (3) are held together by control wires (12, 13) whose distal ends are fastened at a distal segment (6a) of the second group (3), and further comprising tensioning wires (14, 15) which run in a proximal direction through a rigid shaft part (4), said tensioning wires (14, 15) having proximal ends which are fixed in a tensioning device (16) inside a handle (7) provided on the shaft.

3. The shaft in accordance with claim 2, wherein the tensioning device (16) comprises a distal seat (18), a proximal seat (17) and the spring (19) that holds the two seats (17, 18) at a distance from each other, whereby the distal seat (18) has threaded region (18a) that is screwed into a counter-thread (7a) in the handle (7), the proximal ends of the tensioning wires (14, 15) being fastened to the proximal seat (17), and distal ends of the tensioning wires (14, 15), running through bores in the segments (6) of the second group (3), and being secured at the distal segment (6a).

4. The Shaft in accordance with claim 2, wherein control wires (10, 11) are fastened at their distal ends to a distal side of a distal segment (5a) of the first group (2).

5. The shaft in accordance with claim 1, wherein said adjusting means comprises two adjusting devices (20, 21) inside the handle (7) for adjusting the respective segments (5, 6) of groups (2, 3) with respective control wires (10, 11; 12, 13).

6. The shaft in accordance with claim 1, wherein segments (5) of the first group (2) have at one end two semi-circular projections (22) and at the other end matching recesses (23), which lie diametrically opposed to each other, the projections (22) of a segment (5) being inserted into the corresponding recesses (23) of a neighboring segment (5), and two neighboring segments (5) being connected with each other in an axially flexible manner.

7. The Shaft in accordance with claim 1, wherein a distal last segment (6a) of the second group (3) in the region of its recess (26) is linked in an axially flexible manner with a projection (22) of a proximal first segment (5) of the first group (2).

8. The shaft in accordance with claim 1, wherein a distal end of a proximally rigid shaft part (4) is provided with a recess (26) for receiving a projection (25) of a proximal first segment (6b) of the second group (3).

9. A shaft in accordance with claim 1, wherein the means for axially linking the segments (6) of the second group (3) further includes a positive linking means for causing said spring (19) to apply a sufficient force to positively lock said segments (6) relative to one another.

10. A shaft in accordance with claim 1, wherein the means for axially linking the segments (6) of the second group (3) further includes a non-positive linking means for causing said spring (19) to apply a sufficient force to non-positively lock said segments (6) relative to one another.

11. A shaft (1) for guiding medical instruments, particularly for guiding instruments into a body cavity, comprising at least a first group (2) of neighboring segments (5) and a second group (3) of neighboring segments (6), said segments (5, 6) being hollow on their insides, control wires (10, 11; 12, 13) connected respectively to said first and second group, for adjusting positions of said segments, and means for adjusting the segments of one group independently of another group, said shaft having distal and proximal end regions, the segments (5) of the first group (2) being provided in the distal end region and being flexibly linked with each other, the segments (6) of the second group (3) being provided proximally of the first group (2) and including means for axially linking the segments (6) of the second group (3) together, and a spring (19) connected to segments (6) of the second group (3) and having variably adjustable force for tensioning the segments (6) of the second group (3), whereby the positions of the segments (5,6) may be set to form various curvatures of the shaft, and wherein the segments (6) of the second group (3) have at one end projections (25) that are essentially semicircular and diametrically opposed to one another and whose circumference is formed in the shape of a wavy line, and at the other end semicircular recesses (26), and further comprising a lock pin (29) in the recess of each segment (6), said lock pin being located in the middle of a bowed surface which forms the semicircular recess (26), said lock pin locking into the wavy-line shaped projections (25) of a neighboring segment (6).

12. The shaft in accordance with claim 11 wherein the segments (6) of the second group (3) are held together by means of control wires (12, 13) whose distal ends are fastened at a distal segment (6a) of the second group (3), and further comprising tensioning wires (14, 15) which run in a proximal direction through a rigid shaft part (4), said tensioning wires (14, 15) having proximal ends which are fixed in a tensioning device (16) inside a handle (7) provided on the shaft.

13. The shaft in accordance with claim 12, wherein control wires (10, 11) are fastened at their distal ends to a distal side of a distal segment (5a) of the first group (2).

14. The shaft in accordance with claim 12, wherein the tensioning device (16) comprises a distal seat (18), a proximal seat (17) and the spring (19) that holds the two seats (17, 18) at a distance from each other, whereby the distal seat (18) has threaded region (18a) that is screwed into a counter-thread (7a) in the handle (7), the proximal ends of the tensioning wires (14, 15) being fastened to the proximal seat (17), and distal ends of the tensioning wires (14, 15), running through bores in the segments (6) of the second group (3), and being secured at the distal segment (6a).

15. The shaft in accordance with claim 11, wherein said adjusting means comprises two adjusting devices (20, 21) inside the handle (7) for adjusting the respective segments (5, 6) of groups (2, 3) with respective control wires (10, 11; 12, 13).

16. The shaft in accordance with claim 11, wherein segments (5) of the first group (2) have at one end two semi-circular projections (22) and at the other end matching recesses (23), which lie diametrically opposed to each other, the projections (22) of a segment (5) being inserted into the corresponding recesses (23) of a neighboring segment (5), and two neighboring segments (5) being connected with each other in an axially flexible manner.

17. The shaft in accordance with claim 11, wherein a distal last segment (6a) of the second group (3) in the region of its recess (26) is linked in an axially flexible manner with a projection (22) of a proximal first segment (5) of the first group (2).

18. The shaft in accordance with claim 11, wherein a distal end of a proximally rigid shaft part (4) is provided with a recess (26) for receiving a projection (25) of a proximal first segment (6b) of the second group (3).

19. A shaft in accordance with claim 1, wherein the means for axially linking the segments (6) of the second group (3) further includes a positive linking means for causing said spring (19) to apply a sufficient force to positively lock said segments (6) relative to one another.

20. A shaft in accordance with claim 11, wherein the means for axially linking the segments (6) of the second group (3) further includes a non-positive linking means for causing said spring (19) to apply a sufficient force to non-positively lock said segments (6) relative to one another.

* * * * *